(12) United States Patent
Sadan

(10) Patent No.: US 12,350,001 B2
(45) Date of Patent: Jul. 8, 2025

(54) SYSTEM AND METHOD FOR CATHETERIZATION USING AN INTRALUMINAL ELECTROMAGNETIC WORKING CAPSULE

(71) Applicant: NIVAT MEDICAL DEVICE LTD., Kfar Tavor (IL)

(72) Inventor: Nir Sadan, Afula (IL)

(73) Assignee: NIVAT MEDICAL DEVICE LTD., Kfar Tavor (IL)

( * ) Notice: Subject to any disclaimer, the term of this patent is extended or adjusted under 35 U.S.C. 154(b) by 279 days.

(21) Appl. No.: 17/898,731

(22) Filed: Aug. 30, 2022

(65) Prior Publication Data

US 2022/0409316 A1 Dec. 29, 2022

Related U.S. Application Data

(62) Division of application No. 16/351,560, filed on Mar. 13, 2019, now Pat. No. 11,583,355.

(30) Foreign Application Priority Data

Mar. 22, 2018 (IL) .......................... 258323

(51) Int. Cl.
*A61B 34/00* (2016.01)
*A61B 1/00* (2006.01)
(Continued)

(52) U.S. Cl.
CPC .......... *A61B 34/73* (2016.02); *A61B 1/00016* (2013.01); *A61B 1/041* (2013.01);
(Continued)

(58) Field of Classification Search
CPC ... A61B 1/00016; A61B 1/041; A61B 1/0661; A61B 1/3137; A61B 34/73;
(Continued)

(56) References Cited

U.S. PATENT DOCUMENTS 4,389,208 A 6/1983 Leveen et al.
6,165,209 A * 12/2000 Patterson .................. A61F 2/95
623/1.1
(Continued)

FOREIGN PATENT DOCUMENTS

CN 1893990 A 1/2007
CN 101961261 A 2/2011
(Continued)

OTHER PUBLICATIONS

Tognareli, S., et al. 2012. "Magnetic propulsion and ultrasound tracking of endovascular devices", Journal of Robotic Surgery, 6(1): 5-12. DOI 10.1007/s11701-011-0332-1.
(Continued)

*Primary Examiner* — Sarah A Long
*Assistant Examiner* — Raihan R Khandker
(74) *Attorney, Agent, or Firm* — The Roy Gross Law Firm, LLC; Roy D. Gross

(57) ABSTRACT

There is provided a system for cardiac electromagnetic/magnetic catheterization for diagnosing and treating blood vessels of a patient. The system having at least one electromagnetic intraluminal capsule able to force its way through a narrowing blood vessel, the capsule carrying a camera allowing visualization of blood vessels of a patient. There is a portable electromagnetic tip, where the tip pulls the electromagnetic capsule by electromagnetic force, and when the magnetic tip moves along a body of a patient and pulls the intraluminal electromagnetic capsule along with it towards a narrowing blood vessel visualized by the camera, so that the capsule then treats the narrowing site and clears the blood vessel from coronary plaque. In addition working capsule can replace diseased valve in any cardiac position for either temporary or permanent needs.

21 Claims, 12 Drawing Sheets

(51) Int. Cl.
*A61B 1/04* (2006.01)
*A61B 1/06* (2006.01)
*A61B 1/313* (2006.01)
*A61B 17/22* (2006.01)
*A61B 17/3207* (2006.01)
*A61B 90/00* (2016.01)
*A61F 2/01* (2006.01)
*A61F 2/24* (2006.01)
*A61F 2/95* (2013.01)
*A61M 25/01* (2006.01)

(52) U.S. Cl.
CPC .......... *A61B 1/0661* (2013.01); *A61B 1/3137* (2013.01); *A61B 17/2202* (2013.01); *A61B 17/3207* (2013.01); *A61F 2/013* (2013.01); *A61F 2/243* (2013.01); *A61M 25/0125* (2013.01); *A61M 25/0127* (2013.01); *A61B 2090/373* (2016.02); *A61F 2002/9505* (2013.01)

(58) Field of Classification Search
CPC ............ A61B 17/2202; A61B 17/3207; A61B 1/00158; A61B 1/00148
See application file for complete search history.

(56) References Cited

U.S. PATENT DOCUMENTS

| | | | |
|---|---|---|---|
| 8,235,055 | B2 | 8/2012 | Mintchev et al. |
| 9,814,433 | B2 | 11/2017 | Benishti et al. |
| 2003/0020810 | A1 | 1/2003 | Takizawa et al. |
| 2003/0216622 | A1 | 11/2003 | Meron et al. |
| 2004/0030454 | A1* | 2/2004 | Kim .................. A61B 1/00156 700/245 |
| 2004/0147939 | A1* | 7/2004 | Rabkin ................ A61B 17/221 623/1.11 |
| 2008/0033569 | A1* | 2/2008 | Ferren .................. A61B 5/4839 623/23.7 |
| 2011/0065988 | A1* | 3/2011 | Eidenschink .......... A61B 1/267 600/115 |
| 2012/0035437 | A1 | 2/2012 | Ferren et al. |
| 2015/0141750 | A1 | 5/2015 | Iddan et al. |
| 2018/0296289 | A1* | 10/2018 | Rodriguez-Navarro ..................... A61B 90/361 |
| 2019/0000625 | A1* | 1/2019 | O'Carroll ........ A61B 17/07207 |
| 2019/0282074 | A1 | 9/2019 | Duan et al. |

FOREIGN PATENT DOCUMENTS

| | | |
|---|---|---|
| CN | 104093445 A | 10/2014 |
| CN | 106029931 A | 10/2016 |
| DE | 10161958 A1 | 7/2003 |
| KR | 20090122648 A | 12/2009 |
| KR | 101524552 B1 | 5/2015 |
| WO | 2003090618 A2 | 11/2003 |
| WO | 2009145405 A1 | 12/2009 |

OTHER PUBLICATIONS

European Search Report for European Patent Application No. EP19164746.0, completed Jan. 8, 2020, 5pp.

Israeli Office Action for Israeli Application No. 258323, dated Jan. 1, 2019, 7pp.

Israeli Search Report for Israeli Application No. 258323, dated Jan. 1, 2019, 5pp.

* cited by examiner

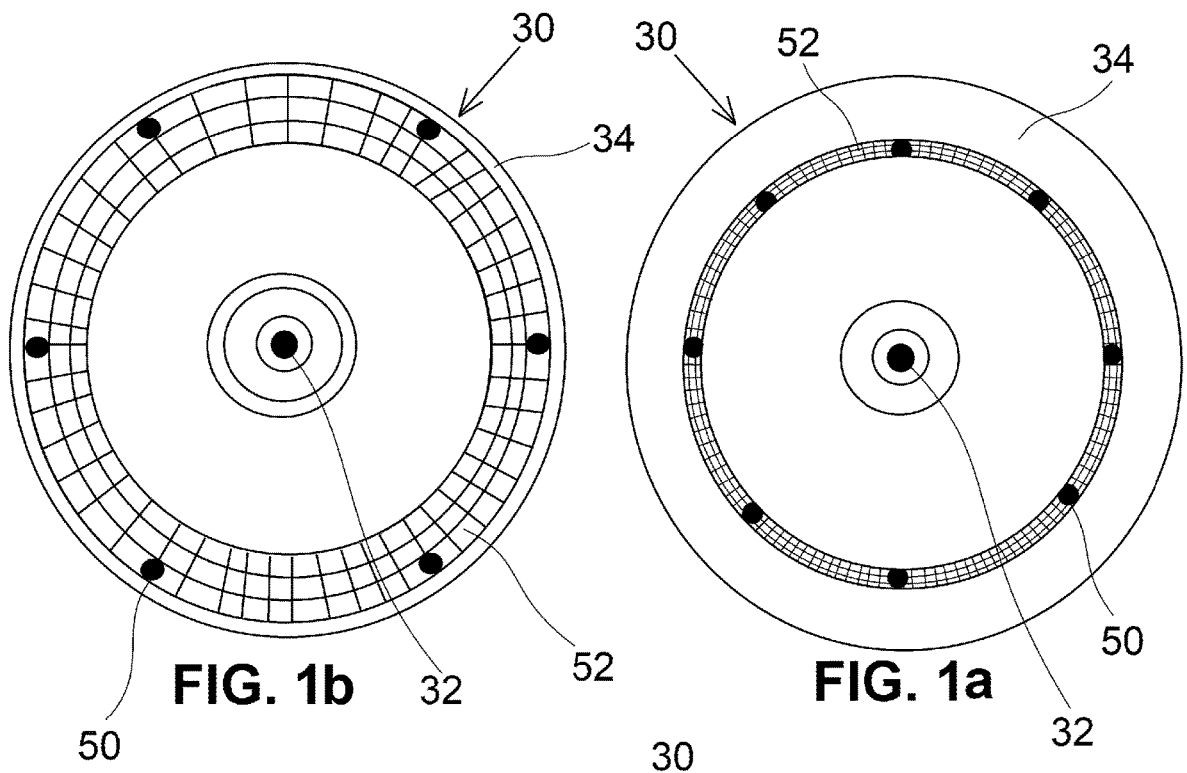
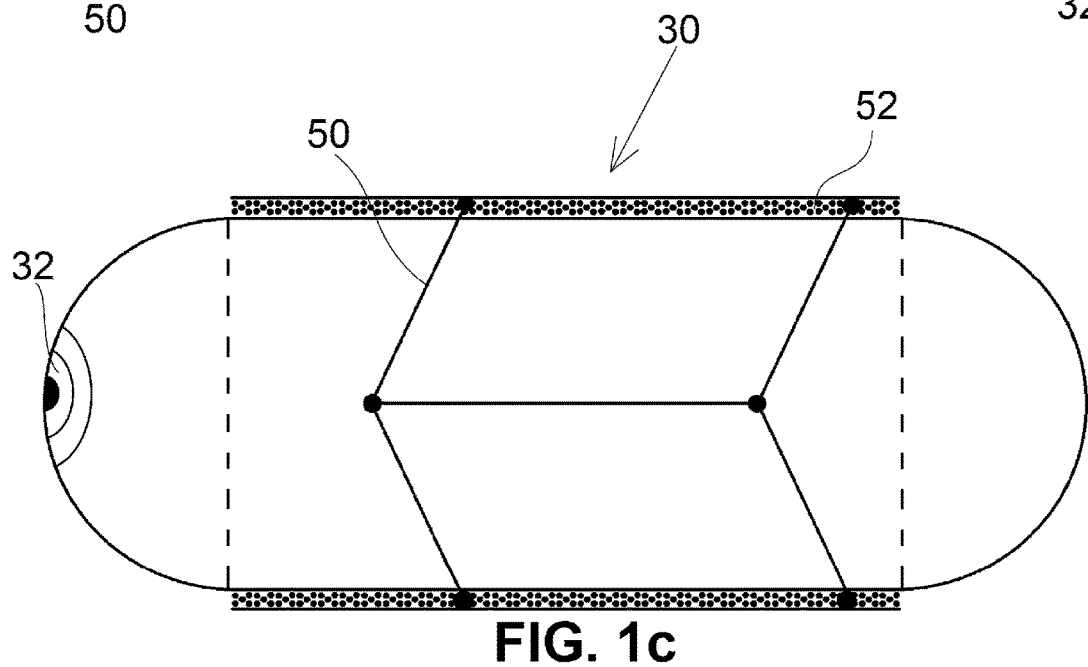

SYSTEM AND METHOD FOR CATHETERIZATION USING AN INTRALUMINAL ELECTROMAGNETIC WORKING CAPSULE

CROSS REFERENCE TO RELATED APPLICATIONS

This application is a U.S. Divisional application of U.S. patent application Ser. No. 16/351,560, filed Mar. 13, 2019, which claims the benefit of priority of Israeli Patent Application No. 258323 filed Mar. 22, 2018, the contents of which are all incorporated herein by reference in their entirety.

TECHNICAL FIELD

The present invention relates to the field of cardiac catheterization. More particularly, the invention relates to an intraluminal magnetic capsule.

BACKGROUND ART

More than a million cardiac catheterizations are performed each year in the United States. Several approaches to cardiac catheterization have been developed over the past 60 years.

Catheterization is done in order to confirm the presence of suspected coronary artery disease (CAD) and define its anatomical location and severity. Once the catheterization is being performed and CAD has been confirmed, cardiac surgery, angioplasty or stenting may be performed.

The two most widely used techniques for cardiac catheterization involve access through the femoral or radial artery, or rarely, brachial artery.

Traditionally, the heart has been accessed via the femoral artery; however, in the last 2 decades, the radial artery has been more widely used, since it (1) is easily accessible (even in obese individuals), (2) is the preferred site of access by many patients, (3) is associated with a lower incidence of port of entry related complication and (4) allows earlier ambulation of the patient following the procedure than a femoral catheterization.

There are some disadvantages to the regularly used procedure: many potential complications may occur in, such as abrupt vessel closure leading to myocardial infarction, bleeding, vessel perforation, thrombosis, and more.

In addition, some patients cannot be catheterized since they are allergic to contrast dye which is used during an Angiogram, or some have a kidney disease that does not allow the administration of contrast dye. Furthermore, X-rays irradiation has a hazardous effect to both the patient and the medical team.

More specifically, the traditional technique using catheters and wires in blood vessels from long distance (over 100 cm) has multiple limitations such as: 1. Difficulty in navigation, 2. Poor effective pushing and penetrating forces due to both long distance and soft tip wires. On the other hand, by using rigid edges there is a potential cause for vessel perforation.

The basic therapeutic approach for blood vessel narrowing nowadays is done by using balloons made of different materials-compliant or non compliant, etc. All the balloons create temporary vessel occlusion, which may aggravate myocardial ischemia, cause vessel wall damage and potential side branch block. These complications may lead to peri procedure, myocardial infarctions or in extreme cases even death.

Several approaches exist to solve the variety of the above mentioned risks and disadvantages associated with cardiac catheterization. For example, U.S. Pat. No. 8,235,055 to Mintchev. None of them teach a technique which doesn't rely on pushing the catheter from a large distance from the heart all the way to the heart.

DE10161958 and Tognarelli et. Al. 2012 Magnetic propulsion and ultrasound tracking of endovascular devices of Journal of robotic surgery, 6(1) pp 5-12 disclose magnetic transporting of a capsule. CN101961261 discloses filtering by a capsule. KR101524552 discloses rotating drilling outwards, however not to walls of a blood vessel. U.S. Pat. No. 9,814,433 discloses catheterization.

However, none of the above discloses a replacement to the broadening balloon.

Therefore, there is a need to provide satisfactory solutions to the aforementioned problems.

SUMMARY OF THE INVENTION

The new system for diagnosing and treating vascular pathology based on 3 steps:
1. Creating a road mapping angiography by using intravascular capsule camera.
2. Using electromagnetic/magnetic forces for navigating capsule towards the target pathology
3. This technique use different working capsules for different pathologies such as:
    A—blood vessel narrowing, crossing total occlusion (CTO)
    B—vessel wall shaving and stenting
    C—treating varieties of valvular pathologies
    D—On principle, single capsule has the ability to perform multiple functions: vibration, shaving, vessel dilatation, and distal protection (by filtering).
1. First capsule able to force its way through the blood vessel, carrying a camera allowing visualization of blood vessels of a patient. This capsule provide the physician the first road mapping angiography. After providing road map this capsule will park down stream the artery and become a protective filter. Every parking process is controlled by external signal which change the capsule diameter, thus enable adherence to the vessel wall,
A portable electromagnetic tip, wherein said tip pulls the capsule by electromagnetic/magnetic force along the created road mapping angiography towards the target vascular bed.

The system pulls the electromagnetic capsule by electromagnetic force using the principles of Magnetic Levitation (MagLev principle).

The pulling force of the magnetic tip is far greater than the pushing force produced by the standard catheterization technique. The pulling force makes it possible for the capsule to penetrate tight or occluded vessels combined with the basic function of the working capsule.

Working Capsules:
3A
The first capsule (No 1) has viewing capabilities, vessel dilation, vibration movements and filter function.
   For dilating blood vessel, the capsule enables to change its diameter by electric DC nano motor for eliminating the narrowing.
   In case of total block (CTO-chronic total occlusion), the pulling forces of the system will increase. Parallel to it an internal vibrator system, can be activated. This system increases the chances of penetration (similar to drilling in a concrete with or without vibration) and creating first channel in the presence of CTO.

3B

In the presence of calcific or highly fibrotic lesion the working capsule may shave the plaque (No 2). Last capsule (No 3) can implant stent in the target vessel. In contrast to the balloon dilatation technique (blocking blood flow), the working capsule enables blood flow in each step of its activity.

3C

Capsules for Valvular Lesions

BACKGROUND

In western countries the incidence of valvular pathologies increases with age. Valvular pathologies may lead to acute or chronic heart failure.

The main etiologies are ischemic heart disease and degenerative disorders which affect different components of valve structure. Pulmonary hypertension from any cause may lead to right sided tricuspid regurgitation.

The major obstacles and limitation for therapy in these patients are the co-existence of additional comorbidities, ventricular dysfunction and the presence of severe coronary artery disease.

Nowadays 30-40% from adult population who need therapeutic solution are rejected and refused by heart surgeons. Our daily practice raises the need for temporary valve solution in order to stabilize and improve patient's cardiac status. Unfortunately, there is no system for temporary valve need nowadays.

Adult population who suffer from age related aortic stenosis are treated by endovascular technique (TAVR) using either balloon or self-expandable systems. The main limitations of the actual system are difficulties in valve position, non-ideal adherent of the new valve in the new position leading to high percentage of peri valvular leakages. Use of stiff wires may cause damage to blood vessels or cardiac chambers, In the presence of the actual systems once we release the valve we can't retract it or re adjust its position.

In case of tissue leaflet destruction (Biological valve) the only solution of the actual system is valve in valve procedure.

Our working capsule for valve disorder gives several solutions for several valvular issues:

1. By using our valve capsule we can mplant biological valve in both left and right heart position for both permanent or temporary needs.
2. Valve capsule navigation, position and opening are fully controlled by external operator using a pointing device, such as by main joystick lead. Valve frame opening/closing, and adaptation in the destination segment will be conducted by internal Nano motor build in the capsule. This fine tuning adjustment will prevent peri valvular leakages.
3. Valve capsule can be adjusted to different valve diameters (20-37 mm) and in any time can be retractable. This advantage can be adopted mainly to grown kids who need valve replacement parallel to age related anatomic changes contrary to the actual system in case of leaflet tissue dysfunction our capsule can be retracted, removed and a new valve capsule can be implanted.
4. The basic structure of the valvular capsule integrates large fields camera which show on line valve function and potential para valvular leakage.
5. In case of any structural or functional failure the implanted valve capsule can be replaced by a new valve capsule

BRIEF DESCRIPTION OF DRAWINGS

Preferred embodiments, features, aspects and advantages of the present invention are described herein in conjunction with the following drawings:

FIGS. 1a-c show front, rear and side views of an electromagnetic capsule according to a preferred embodiment of the present invention;

Figure 10A:
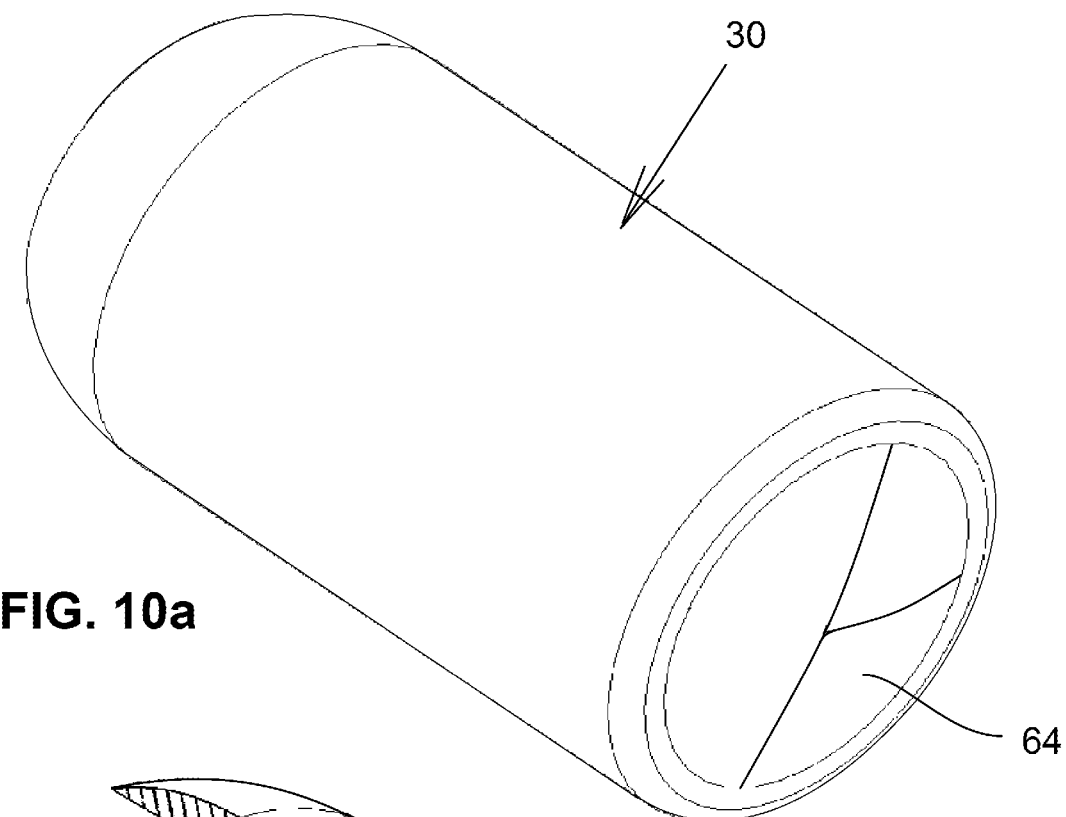
Figure 10B:
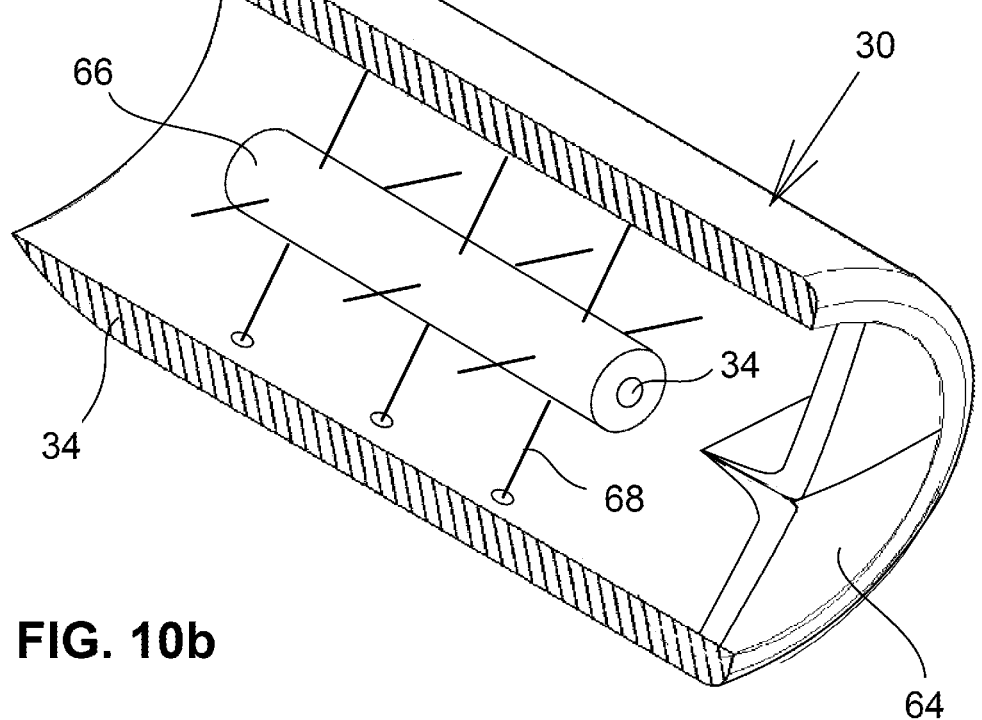

Each of FIGS. 10a and 10b schematically illustrates a capsule used as a cardiac valve, according to a further embodiment of the invention.

Figure 11A:
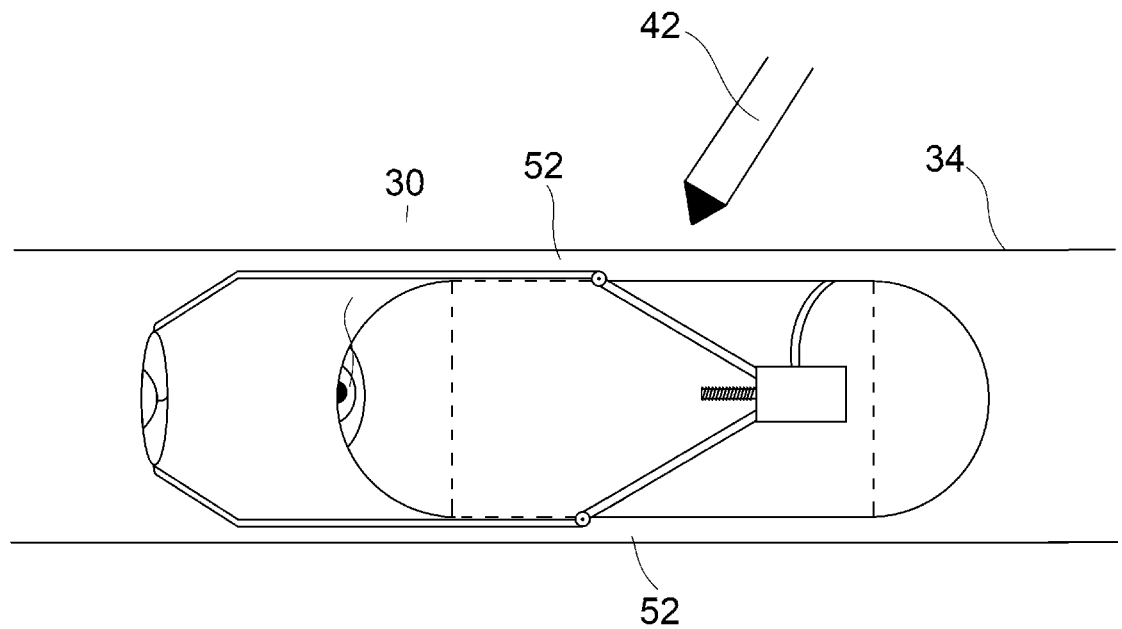

FIG. 11a is a longitudinal-sectioned view of the capsule when being moved.

Figure 11B:
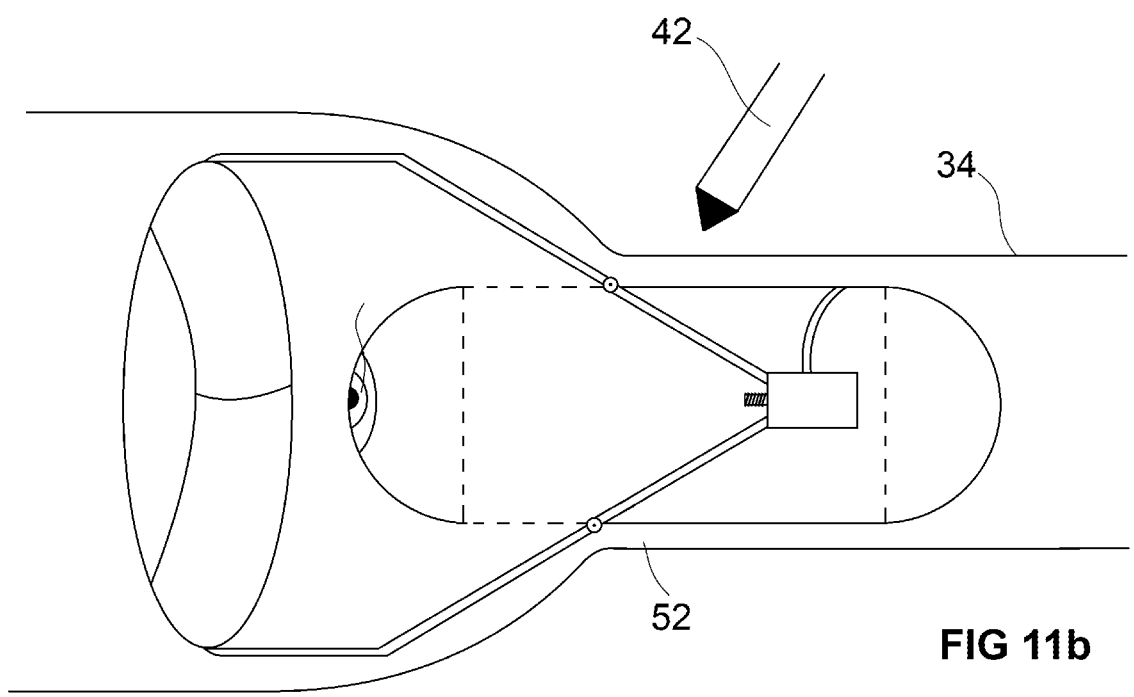

FIG. 11b is a longitudinal-sectioned view of the capsule when its supporting poles open in order to be fixed in the current position of the capsule.

It should be understood that the drawings are not necessarily drawn to scale.

DESCRIPTION CSF EMBODIMENTS

The present invention will be understood from the following detailed description of preferred embodiments ("best mode"), which are meant to be descriptive and not limiting. For the sake of brevity, some well-known features, methods, systems, procedures, components, circuits, and so on, are not described in detail.

Referring now to FIG. 1a, there is shown a front view of a first electromagnetic intraluminal capsule 30, in a folded configuration, having a camera 32 at the front, and a protective filter 52. First capsule 30 is introduced into the blood vessel 34 of a patient 36 by injection, after beginning a catheterization procedure as any standard catheterization.

FIG. 1b shows a front view of first capsule 30 in an open configuration.

FIG. 1c shows a side view of first capsule 30.

Capsule 30 may carry more than one camera. 32, and additional camera 32 (not shown) may be located on the rear of capsule 30. The size of camera 32 is between 1 to 5 mm.

Figure 2:
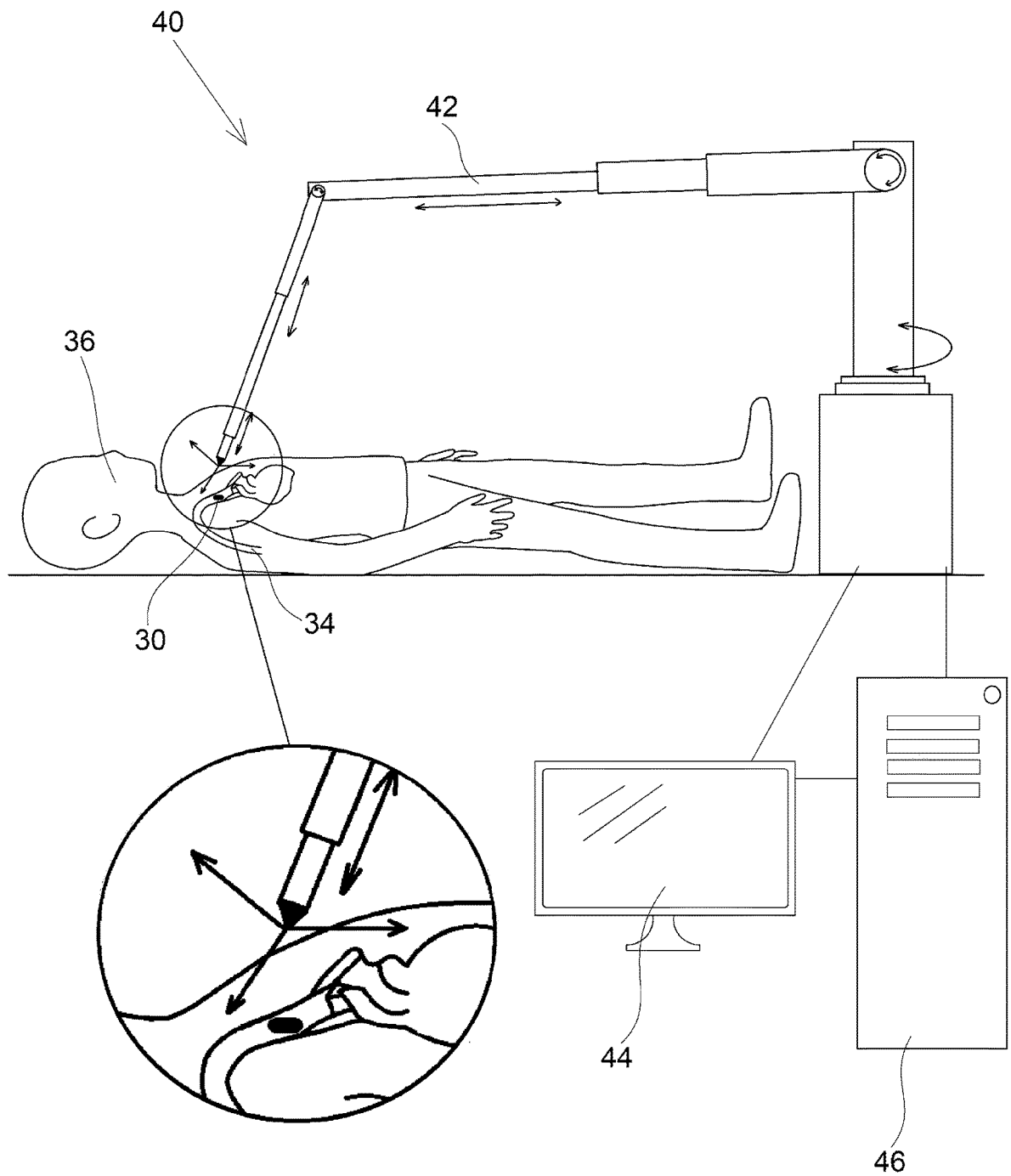
FIG. 2 shows a catheterization system according to a preferred embodiment of the present invention.

Referring now to FIG. 2, there is shown a patient 36 undergoing a catheterization procedure according to the preferred embodiment of the present invention, by a system for cardiac electromagnetic catheterization 40. First magnetic capsule 30 is lodged in patient's 36 blood vessel 34 and a magnetic tip 42 pulls first magnetic capsule 30 along vessel 34 in search for a possible narrowing site 48 (shown in FIG. 3B). Magnetic tip 42 pulls first capsule 30 by electromagnetic force using the principles of Magnetic Levitation (MagLev). The pulling force of magnetic tip 42 is far greater than the force applied by pushing a catheter into a blood vessel, as done in standard catheterization procedures. If an occlusion is rigid and complex (such as a type C lesion), a wire may not be able to penetrate it and then the occluded blood vessel cannot be treated. By using pulling force, first capsule 30 can penetrate also very rigid occlusions so that the blood vessel 34 can be treated. First capsule 30 has a vibrating engine that generates a vibrating motion which assists capsule 30 in penetrating vessel narrowing 48. This is especially essential and useful for tight narrowings that are difficult to penetrate. The vibrating motion is defined by the electrical current of the engine: less current leads to slower speed which then leads to a larger amplitude, and vise versa.

The entire journey of capsule 30 is visualized through camera 32 positioned on its front, and seen on screen 44, thus providing road mapping of the blood vessels of the patient 36. The use of camera 32 makes it unnecessary to use contrasting dyes which are normally used to visualize the arteries, and are used with X-rays which are potentially hazardous to the health of both patient and medical staff. Furthermore, some patients may be allergic to the contrasting dye, or may have a kidney disease and for them using contrasting dye is not an option. Computer 46 commands the movement of tip 42, which may be done via a joystick, for example.

The size of first capsule 30 may vary so that different sized capsules 30 may be used for different circumstances.

Figure 3A:
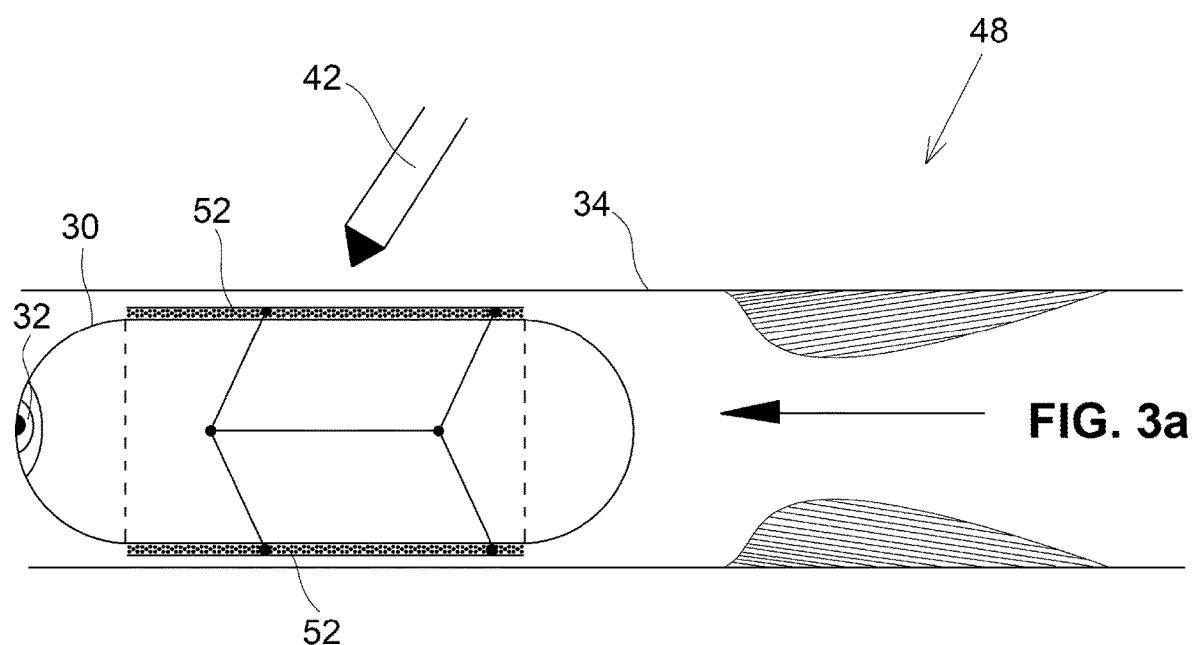
FIG. 3A shows a first capsule led by a magnetic tip through a constricted blood vessel.

Referring now to FIG. 3A there is narrowing site 48 which is identified by viewing it on screen 44, the movement of tip 42 is commanded to stop so that first capsule 30 is situated downstream to narrowing site 48. First capsule 30 forces its way through narrowing site 48.

Figure 3B:
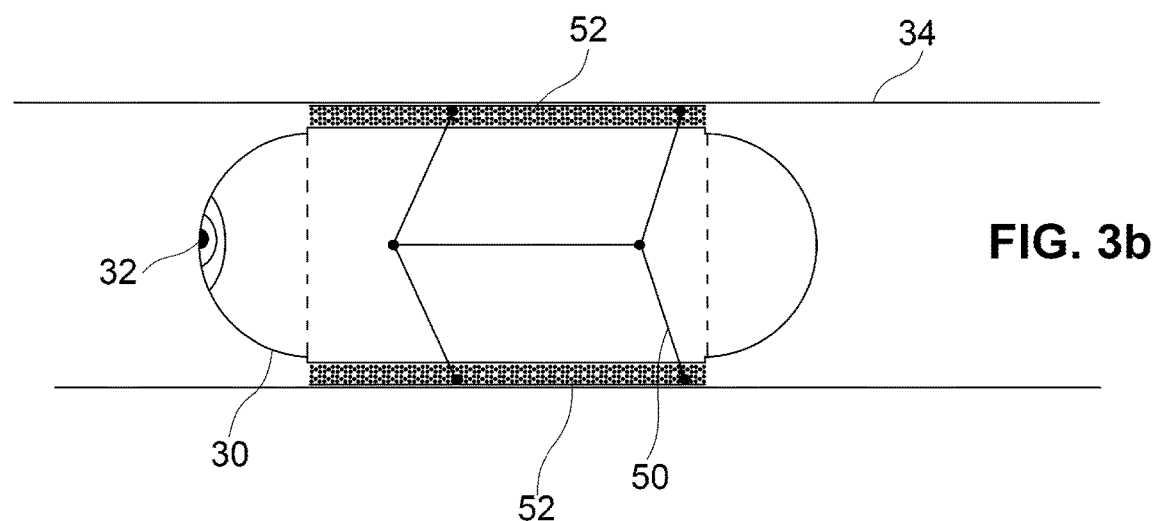
FIG. 3B shows the first capsule deployed and anchored to the blood vessel.

Referring now to FIG. 3B there is shown first capsule 30 in the deployed configuration. First capsule 30 latches onto the diameter of blood vessel 34 via latching means illustrated here by extendable arms 50 which are connected to and controlled by a micro engine (not shown). Extendable arms 50 are folded beneath the exterior of first capsule 30 and are released and spread by the micro engine, Extendable arms 50, when spread, push sections of the exterior of capsule 30 which come in contact with the blood vessel 34 and do not injure it. Extendable arms 50 are connected to sections of protective filter 52 stretched between every two adjacent extendable arms 50, so that when extendable arms 50 are spread to latch onto the wall of blood vessel 34, filter 52 is spread as well (much like an umbrella), and the space between first capsule 30 and the wall of blood vessel 34 is occupied by filter 52. Spread filter 52 decreases somewhat the blood flow, but not in a life-threatening manner Protective filter 52 exists for the purpose of trapping coronary plaque particles which are released from narrowing site 48 downstream to filter 52. Protective filter 52 allows for blood to flow with minimum interruption.

In the known balloon angioplasty procedure for opening a vessel narrowing, the balloon becomes inflated and completely blocks the blood flow, unlike the abovementioned method.

Figure 4A:
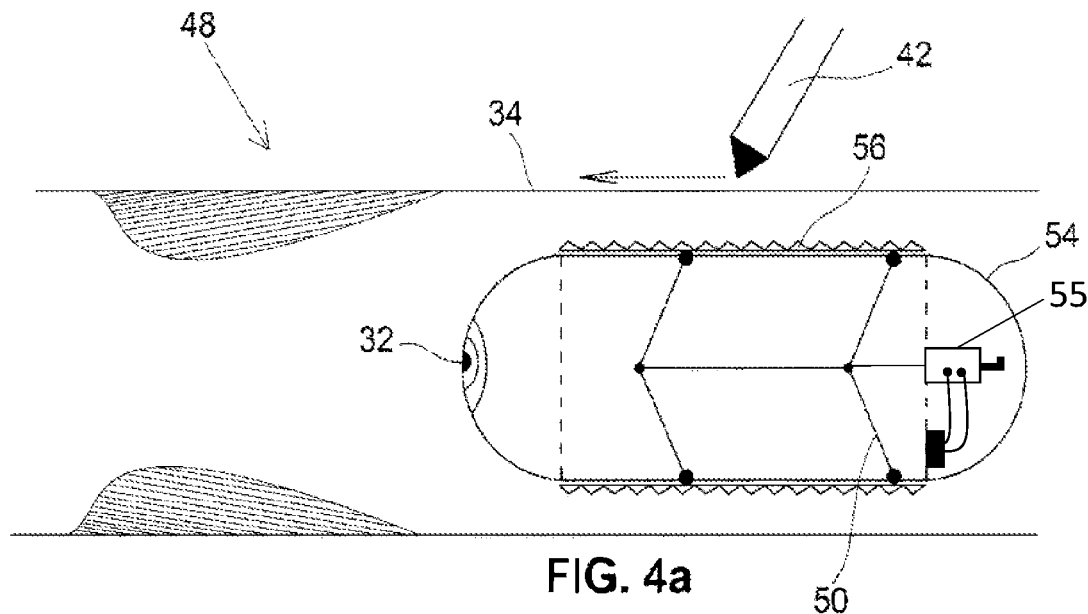
FIG. 4a shows a second capsule led by the magnetic tip to the constricted site
Figure 4B:
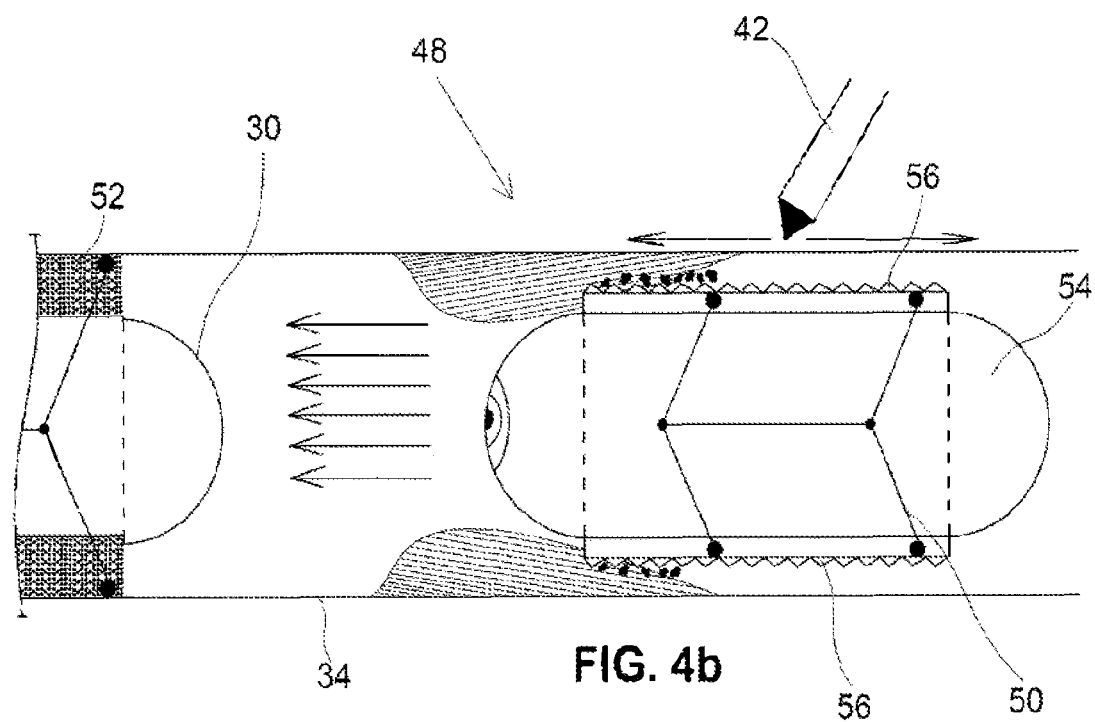
FIG. 4b shows second capsule of FIG. 4a shaving the plaque of the constricted site off the blood vessel walls.

Referring now to FIG. 4a there is shown a second capsule 54 being introduced to blood vessel 34 and brought to occluded site 48 by being pulled by tip 42. Protrusions 56 formed on the surface of second capsule 54 for performing shaving of narrowing site 48 in order to clear blood vessel 34 from plaque 49. Second capsule 54 has a vibrating engine 55 that generates a vibrating motion which assists capsule 54 in shaving the occlusion.

In accordance with some embodiments of the present invention, the vibration engine 55 may be positioned anywhere within the capsule 54.

Second capsule 54 has extendable arms 50 as well as capsule 30, for the option of latching onto blood vessel 34.

The size of second capsule 54 may vary so that different sized capsules 54 may be used for different circumstances.

The shaving process may be viewed by an additional capsule (not shown) carrying a camera so that the medical team performing the catheterization procedure can safely monitor the process and control the movement of tip 42 according to the viewed narrowing site 48. The additional capsule also carries a light adjacent to the camera so that the shaving process can be illuminated and viewed clearly.

Figure 5A:
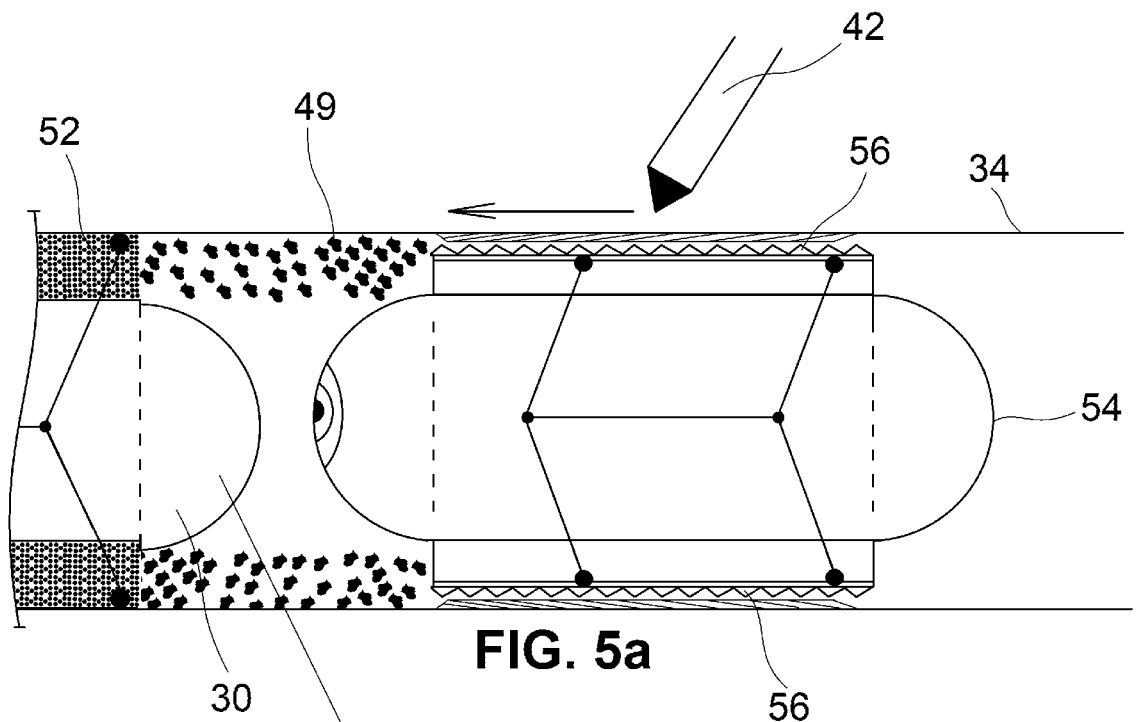
FIG. 5a shows the plaque cleared from the constricted site flow towards the first capsule.

Referring now to FIG. 5a there is shown plaque particles 49 being released from occlusion site 48 by the shaving procedure of second capsule 54. Plaque 49 flows with the blood flow towards first capsule 30 and becomes trapped in protective filter Plaque 49 that is released to the blood stream is likely to block a smaller artery downstream from the treated narrowing site 48, which is liable to lead to cardiac arrest. Protective filter 52 prevents such a scenario.

Figure 5B:
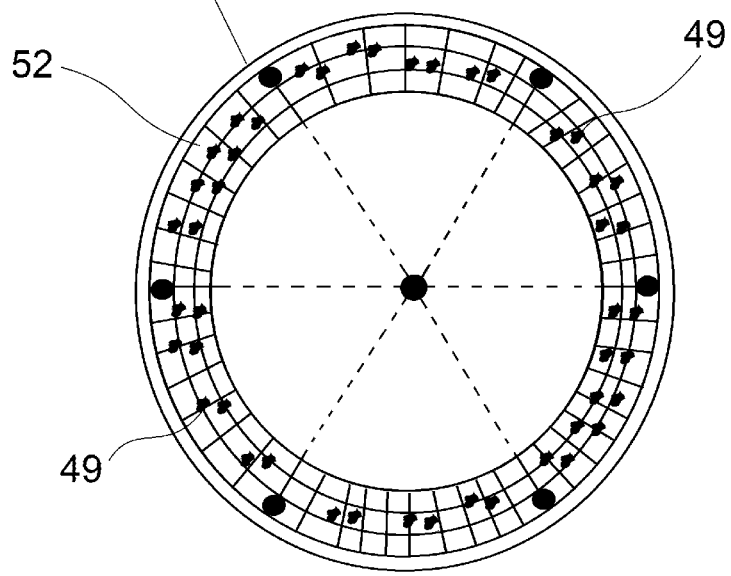
FIG. 5b shows a cross section of the first capsule with plaque captured in its protective filter.

FIG. 5b shows a cross section of first capsule 30 showing plaque 49 trapped in filter 52.

Figure 6:
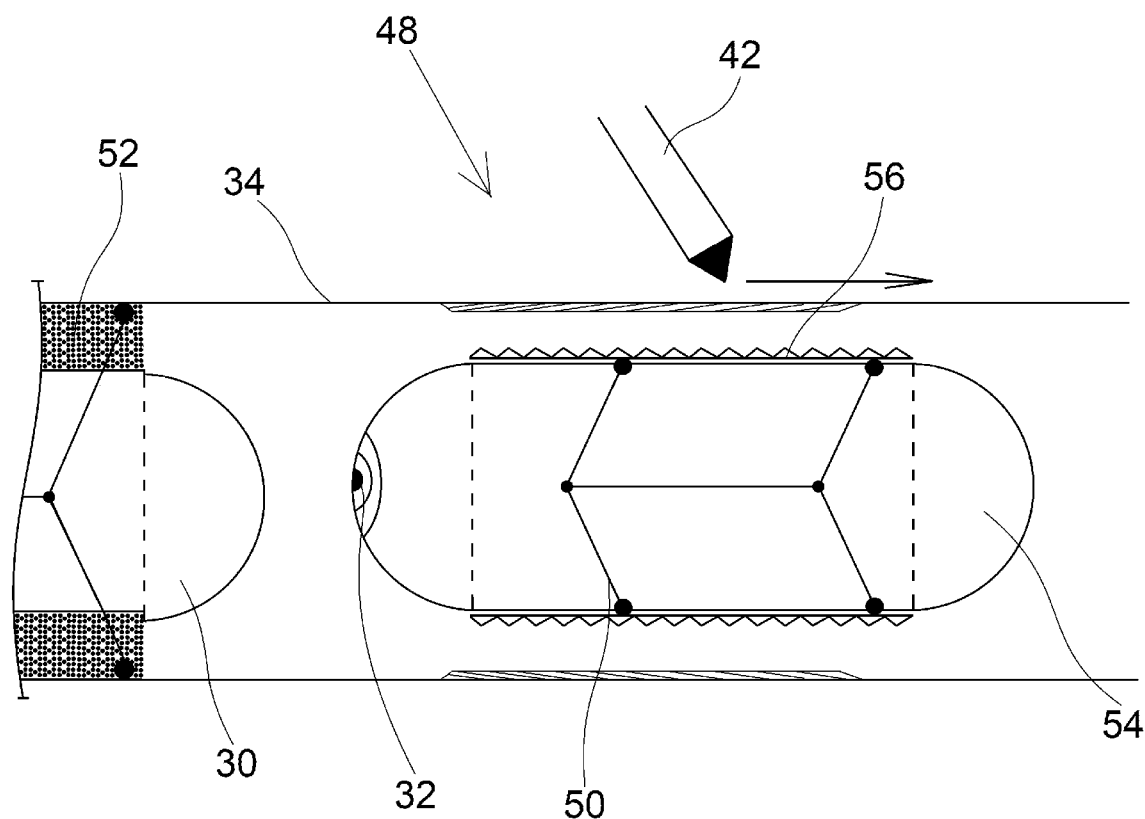
FIG. 6 shows the second capsule being led out of the vessel by the magnetic tip.

Referring now to FIG. 6 there is shown second capsule 54 being removed from treated narrowing site 48 by moving tip 42 pulls second capsule 54.

Figure 7A:
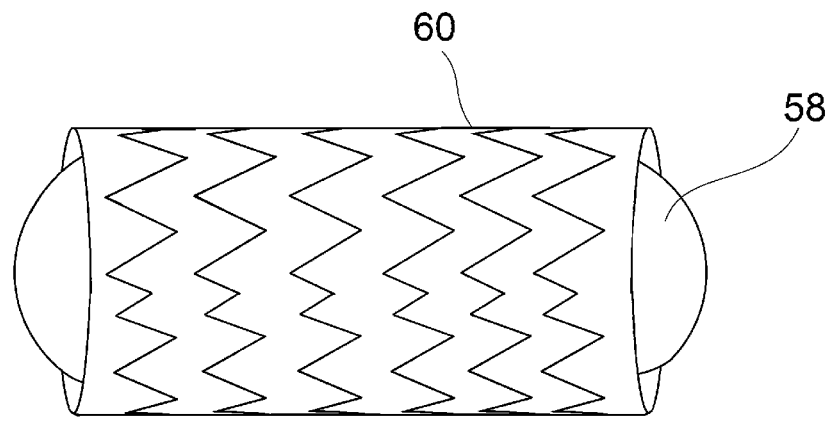
FIGS. 7a-b show a third capsule bearing a stent.
Figure 7B:
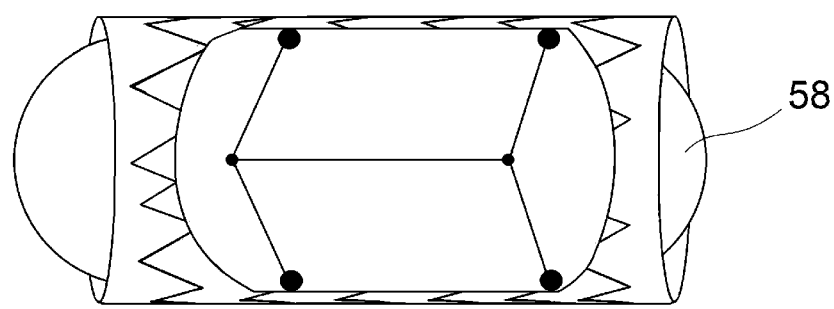

Referring now to FIG. 8 there is shown a third capsule 58 carrying a crimped stent 60 which is to be deployed at treated narrowing site 48 (shown in FIG. 8). In FIG. 7b there is shown a cut out side view of third capsule 58 showing extendable arms 50 which deploy stent 60.

Figure 8A:
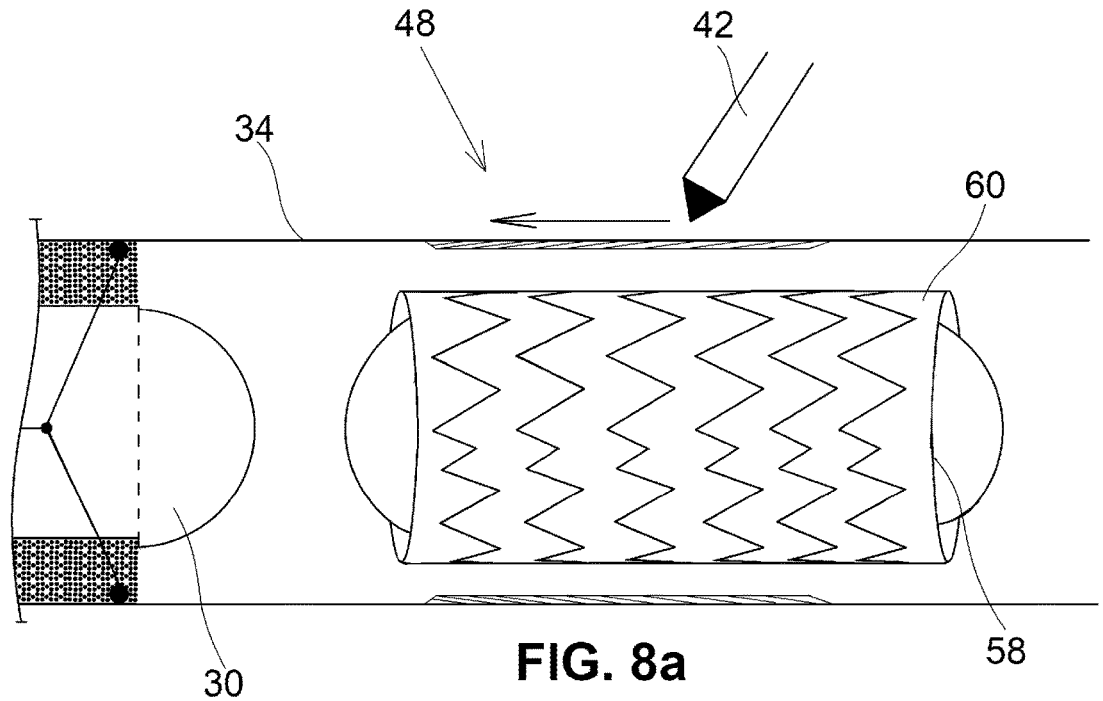
FIG. 8a shows the third capsule being led to the constricted site.

Referring now to FIG. 8a there is shown tip 42 pulling third capsule 58 to the treated narrowing site 48. All the while first capsule 30 is still stationed downstream to the narrowing site 48.

The size of third capsule 58 may vary so that different sized capsules 58 may be used for different circumstances, and for different sized stents 60 to be carried on capsule 58.

Figure 8B:
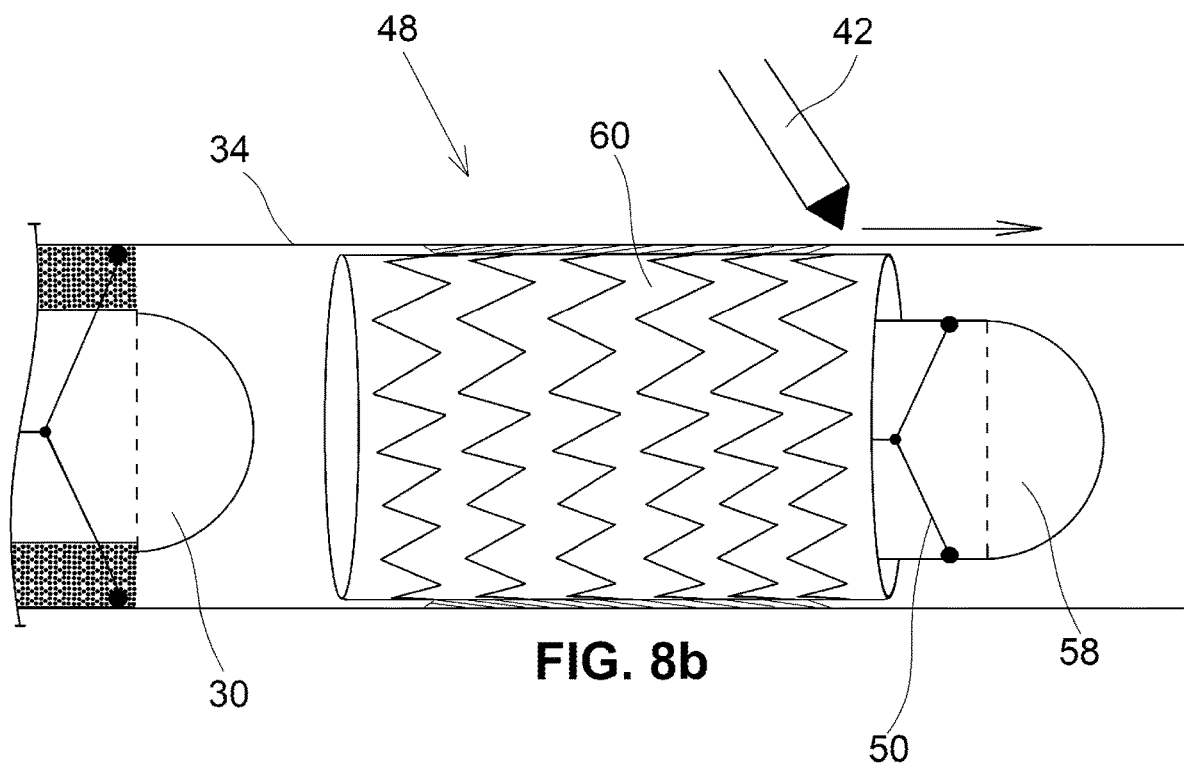
FIG. 8b shows the stent of the third capsule deployed and the third capsule being lead out of the vessel.
Figure 8C:
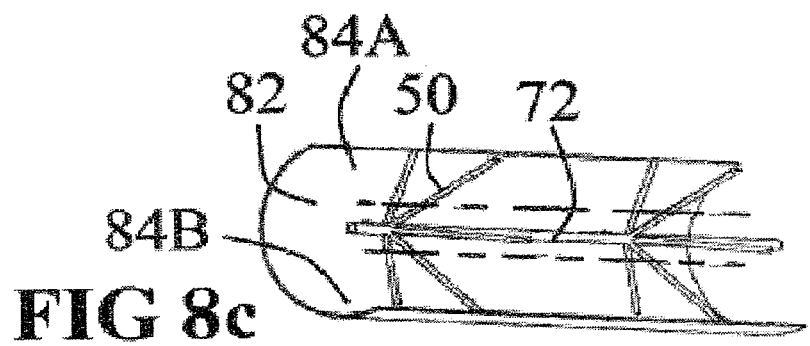
FIG. 8c is a perspective sectional view of the extendable arms and the cylindrical surface surrounding them.
Figure 8D:
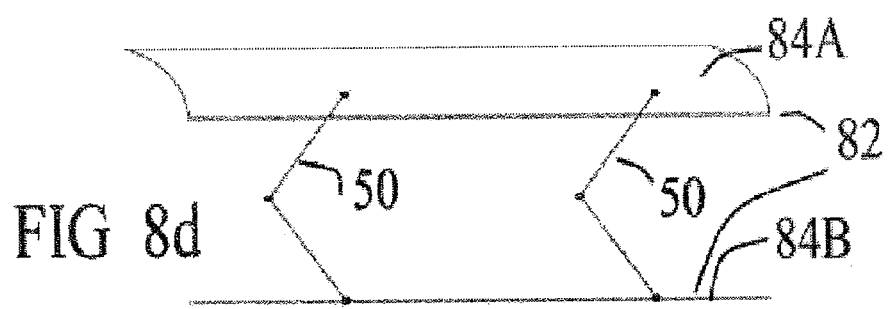
FIG. 8d is a view of the extendable arms and two secondary cylindrical surfaces of the cylindrical surface surrounding them.

FIG. 8b shows stent 60 deployed at occluded site 48 in order to stabilize blood vessel 34 and maintain it. Third capsule 58 is then pulled out of blood vessel 34 and out of the patient's body by tip 42, leaving stent 60. The deployment of stent 60 is done by activating a moving mechanism 78, such as including a motor 70 connected to extendable arms 50 of capsule 30, such as by rotating a thread 72 of capsule 30, thereby spreading extendable arms 50, being surrounded by a cylindrical surface 82 of FIG. 8c and FIG. 8d, which may include rounded elongated pieces 84A, 84B, etc., thereby deploying stent 60 surrounding cylindrical surface 82. The activation of the motor 70 is done by the medical staff using a user interface 74, for transmitting RE 76 controlling motor 70, or any other suitable method.

Preferably three or more rounded elongated pieces 84A, 84B, etc., form together cylindrical surface 82.

Figure 9A:
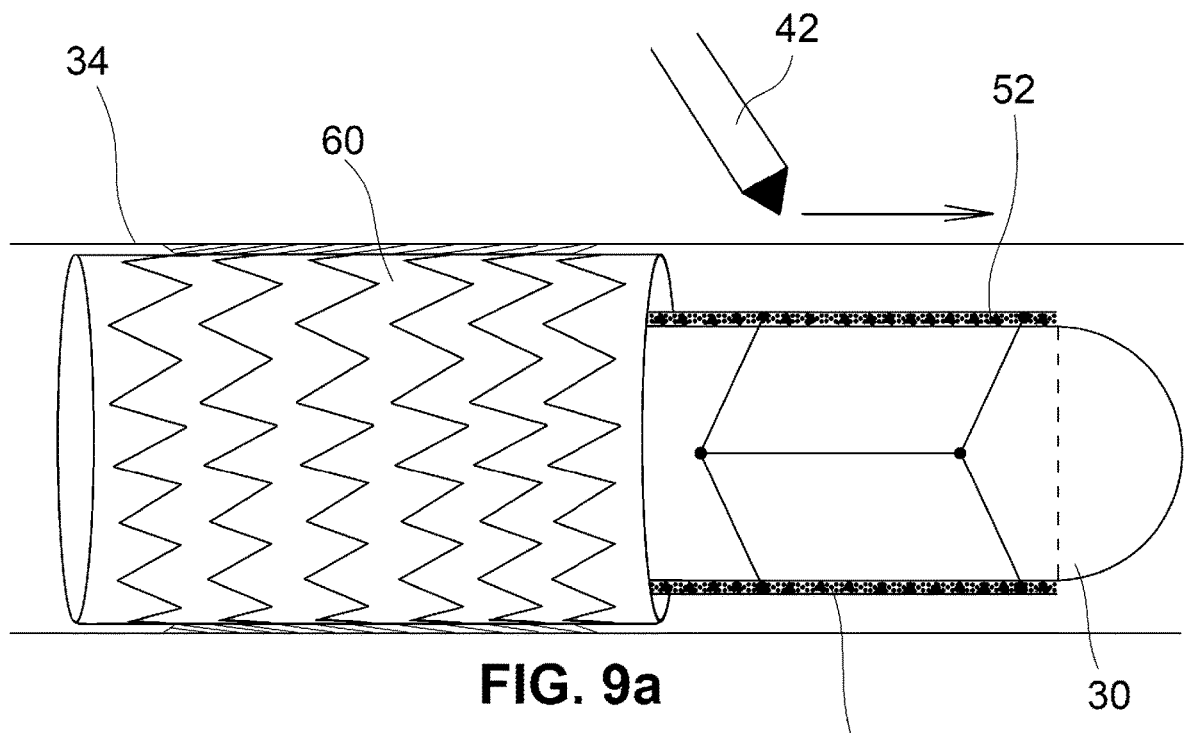
FIG. 9a shows the first capsule being lead out of the vessel after trapping the atheromatous debris.

Referring now to FIG. 9a there is shown first capsule 30 in a collapsed configuration, carrying filter 52 with trapped plaque 49 particles, being pulled out of blood vessel 34 by tip 42, and out of the patient's body.

Figure 9B:
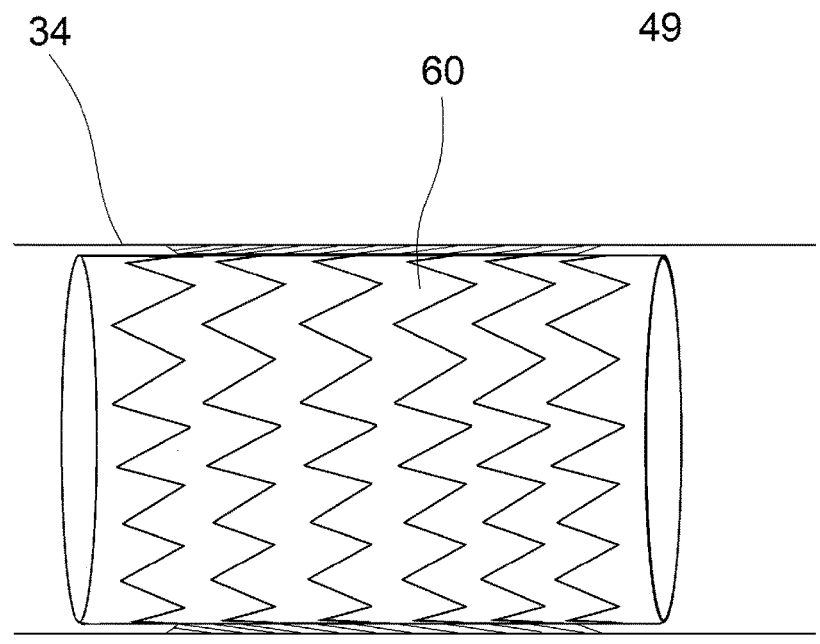
FIG. 9b shows the treated blood vessel having a deployed stent.

Referring now to FIG. 9b there is shown blood vessel 34 with deployed stent 60 supporting it, cleared of plaque 49 and capsules 30, 54, 58.

Each of FIGS. 10a and 10b schematically illustrates a capsule adapted to lie used as a cardiac valve, according to a further embodiment of the invention.

FIG. 10a schematically illustrates a perspective view of the capsule, and FIG. 10b is a sectioned view thereof, which exposes its internal structure.

The capsule is designed to replace a cardiac valve or se a cardiac valve in line with the original hand damaged) cardiac valve of a patient.

The capsule comprises a one-way valve 64 at one end thereof. The capsule's diameter is about 4-7 mm, and the capsule's walls are flexible enough to extend its diameter up to about 35 mm FIGS. 10a and 10b illustrate the capsule in its expanded form. The diameter extension comprises a mechanism suited to this purposes, as described hereinabove. For example, the mechanism can contain an expanding skeleton, such as of an umbrella type mechanism. Reference numeral 68 denotes a supporting pole of the skeleton.

Reference numeral 66 denotes a center that comprises a transceiver for communication with a remote station, a power source, a magnetic element for pulling the capsule, etc. Camera 34 is also installed in center 66. The purpose of the camera is to ease the placement of the capsule in the desired place. The center in this example is in a cylinder form disposed along the capsule. The capsule as a whole is designed to allow free blood flow through the capsule.

The capsule may comprise other means described above, such as a camera 34, wireless communication with a remote control station (not seen in this figure), and so on.

Firstly, the capsule is moved (via magnetic methods described hereinabove) to the heart through the blood vessels leading to the damaged valve. This is possible because of the low diameter, which is about 4-7 mm.

The capsule can be inserted into the opening of the damaged valve of the patient's heart, or placed near the defected cardiac valve, in line to the damaged cardiac valve.

After placing the capsule in or near the damaged cardiac valve, the capsule's diameter expands to about 35 mm by means described hereinabove. If the capsule is inserted into the damaged cardiac valve then the damaged valve seals the passage of the blood and allows its flow only through the capsule. If the capsule is placed near the damaged valve, in line with the valve, it provides proper valve operation, i.e., does not let the blood to flow back.

Preferably, the valve of the capsule is made of an animal tissue, such as of a cow or pig. As mentioned above, the capsule can be placed inside the blood vessels near the infected valve, and in line with the damaged patient's valve. The advantage of this arrangement is that when the capsule needs to be replaced, the damaged cardiac valve can be used as a backup at the time of replacement.

It should be noted that the capsule of the present invention can replace any cardiac valve—the mitral valve, the tricuspid valve, the aortic valve, and the pulmonary valve.

The capsule comprises also means for fixing thereof in a desired location, as described above.

Upon expanding the capsule's diameter, the other end of the capsule opens to allow blood passage therethrough, in one way.

It also should be noted that the diameter of the valve expands along with the expansion of the capsule's diameter.

In the figures and/or description herein, the following reference numerals (Reference Signs List) have been mentioned:

Numeral 30 denotes First capsule
Numeral 32 denotes a camera
Numeral 34 denotes a blood vessel
Numeral 36 denotes a patient
Numeral 40 denotes a system for cardiac electromagnetic catheterization
Numeral 42 denotes a magnetic tip
Numeral 44 denotes a screen
Numeral 46 denotes a Computer
Numeral 48 denotes a narrowing site
Numeral 50 denotes extendable arms
Numeral 51 denotes a cylindrical surface, extendable surrounding, which surround the extendable arms 50
Numeral 52 denotes a protective filter
Numeral 54 denotes a second capsule
Numeral 56 denotes protrusions forming a rough envelope for shaving;
Numeral 58 denotes a third capsule
Numeral 60 denotes a stent
Numeral 64 denotes a one-way valve;
numeral 66 denotes the center of the capsule, and may include mechanisms such as a transceiver, mechanical expansion mechanism of the capsule's diameter, and the like;
numeral 70 denotes the motor/micro engine;
numeral 72 denotes a thread, being a mechanical example for extending and diminishing extendable arms 50;
numeral 74 denotes a user interface;
numeral 76 denotes transmittance for controlling extendable arms 50;
numeral 78 denotes a moving mechanism;
numeral 80 denotes the intima wall of blood vessel 34;
numeral 82 denotes a cylindrical surface surrounding extendable arms 50;
numerals 84A and 84B denote rounded elongated pieces, being secondary cylindrical surfaces of cylindrical surface 82; according to one embodiment, three or more rounded elongated pieces form cylindrical surface 82.

The foregoing description and illustrations of the embodiments of the invention has been presented for the purposes of illustration. It is not intended to be exhaustive or to limit the invention to the above description in any form.

Any term that has been defined above and used in the claims, should be interpreted according to this definition.

The reference numbers in the claims are not a part of the claims, but rather used for facilitating the reading thereof. These reference numbers should not be interpreted as limiting the claims in any form.

The invention claimed is:

1. A capsule configured to be injected into a blood vessel of a patient, the capsule comprising:
   a central portion extending along a longitudinal axis of the capsule;
   an extendable cylindrical surface radially surrounding the central portion and configured to be displaced between a retracted position at which the extendable cylindrical surface lies proximal to the central portion and an extended position at which a whole of the extendable cylindrical surface is spaced from the central portion, wherein the extendable cylindrical surface remains parallel to the longitudinal axis during said displacement between the retracted and extended positions, and the whole of the extendable cylindrical surface extends parallel to the longitudinal axis at both the retracted and extended positions, the extendable cylindrical surface being configured to, at the extended position, contact an intima wall of the blood vessel along an entire length of the extendable cylindrical surface; and a moving mechanism configured to displace the extendable cylindrical surface radially away from the central portion into its extended position and create a space between the central portion and the whole of the extendable cylindrical surface to allow flow of blood therethrough.

2. The capsule according to claim 1, further comprising a stent positioned around the extendable cylindrical surface and configured for being implanted within the blood vessel thereby.

3. The capsule according to claim 2, wherein the moving mechanism is configured to implant the stent within the blood vessel by the displacement of the extendable cylindrical surface into its extended position.

4. The capsule according to claim 1, further comprising an artificial cardiac valve for replacing a patient's damaged cardiac valve.

5. The capsule according to claim 1, further comprising an in-built filter for trapping coronary plaque particles within the blood vessel; and wherein the filter is configured to be displaced between a contracted state associated with the retracted position of the extendable cylindrical surface and an expanded state associated with the extended position of the extendable cylindrical surface.

6. The capsule according to claim 5, wherein at the expanded state, the filter is positioned within the space to allow the flow of blood therethrough while filtering the blood by trapping the coronary plaque particles therefrom.

7. The capsule according to claim 5, wherein the moving mechanism is configured to displace the filter between its contracted state and expanded state simultaneously with displacement of the extendable cylindrical surface between its retracted position and extended position respectively.

8. The capsule according to claim 1, further comprising a rough envelope surrounding said extendable cylindrical surface, wherein said rough envelope is configured for allowing shaving said intima wall of said blood vessel at the extended position of the extendable cylindrical surface.

9. The capsule according to claim 1, wherein said extendable cylindrical surface has an external surface configured to face the intima wall when the capsule is positioned within the blood vessel, the external surface comprising protrusions configured for, at the extended position of the extendable cylindrical surface, shaving the intima wall to clear said blood vessel from plaque particles.

10. The capsule according to claim 1, further comprising a vibration motor for generating a vibrating motion, thereby causing the capsule to vibrate; and wherein said vibration motor is configured for assisting said capsule in at least one of (a) shaving said intima wall, (b) creating a first channel in the presence of chronic total occlusion (CTO), and (c) filtering plaque from the blood.

11. The capsule according to claim 1, further comprising a camera positioned at the central portion for capturing a view of said blood vessel and transmitting said captured view to a screen.

12. The capsule according to claim 1, further comprising extendable arms engaging the extendable cylindrical surface from within the central portion, said moving mechanism being configured to reversible extend the extendable arms to displace the extendable cylindrical surface between its retracted and extended position.

13. The capsule according to claim 1, wherein said extendable cylindrical surface is constituted by a plurality of discreet elongated pieces, each extending along the longitudinal axis, wherein at the retracted position of the extendable cylindrical surface, the elongated pieces are joined together, and at the extended position of the extendable cylindrical surface, the elongated pieces are separated from each other.

14. The capsule according to claim 1, wherein the moving mechanism is configured to firmly hold the extendable cylindrical surface in its extended position even in the absence of an external force from outside the blood vessel when the capsule is positioned within the blood vessel.

15. The capsule according to claim 1, wherein the capsule is configured, at the extended position of the extendable cylindrical surface, to be held at a location along the blood vessel as a stand-alone element even in the absence of an external force.

16. The capsule according to claim 1, wherein the extendable cylindrical surface is configured to, at the extended position, contact the intima wall of the blood vessel along at least a majority of length of the extendable cylindrical surface.

17. The capsule according to claim 1, wherein the moving mechanism is positioned within the central portion and comprises a motor.

18. The capsule according to claim 1, wherein the moving mechanism is configured to be operated from outside the blood vessel via RF (Radio Frequency) transmission when the capsule is positioned within the blood vessel.

19. The capsule according to claim 1, wherein the capsule is configured to be fixed at a tip of a catheter for being guided within the blood vessel.

20. The capsule according to claim 1, wherein the capsule comprises a ferromagnetic substance, and is configured for being guided within the blood vessel via electro-magnetic force.

21. The capsule according to claim 1, wherein in the retracted position, the extendable cylindrical surface constitutes a continuous external surface.

\* \* \* \* \*